United States Patent [19]
Benony et al.

[11] Patent Number: 5,712,891
[45] Date of Patent: Jan. 27, 1998

[54] APPARATUS FOR THE ANALYSIS OF A SOLUTION BY X-RAY FLUORESCENCE

[75] Inventors: Gilbert Benony, Pujaut; Dominique Pouyat, Roquemaure; Thierry Davin, Lapalud, all of France

[73] Assignee: Compagnie Generale Des Matieres Nucleaires, Velizy Villacoublay, France

[21] Appl. No.: 747,450

[22] Filed: Nov. 12, 1996

[30] Foreign Application Priority Data

Nov. 15, 1995 [FR] France ................................. 95 13533

[51] Int. Cl.⁶ ......................................... G01N 23/223
[52] U.S. Cl. ........................................ 378/47; 378/45
[58] Field of Search .................................. 378/47, 45

[56] References Cited

U.S. PATENT DOCUMENTS 3,198,944  8/1965  Furbee ........................... 378/47

FOREIGN PATENT DOCUMENTS 2718528  10/1995  France .
1400587   7/1975  United Kingdom .

OTHER PUBLICATIONS

Patent Abstracts of Japan, vol. 002, No. 154, Dec. 1978 & JP 53 122484 (Shimadzu Corp) Oct. 1978.

U.S. Department of Energy, Monsanto Research Corp., Aug. 1984, C.R. Hudgens, "Selection and testing of materials for use in a flow-through liquid sampling cell for X-ray fluorescence analysis of special nuclear materials in dissolver solution".

American Nuclear Society, International Topical Conference, Methods and Applications of Radioanalytical Chemistry, Hawaii, Apr. 1994, "Development of on line energy dispersive X-ray fluorescence to monitor actinide contaminated waste stream".

CEA Cadarache, Cetama, "Non Destructive Analysis", A collection of comunications presented during technical discussion Sep. 29–30, 1993 at the Centre d'etudes, Valduc, Ph. Bienvenu et al., Total reflection X-ray fluorescence spectrometry (TXRF); a future method for the micro-analysis of radioactive samples.

Primary Examiner—Craig E. Church
Attorney, Agent, or Firm—Pearne, Gordon, McCoy & Granger LLP

[57] ABSTRACT

An apparatus for the analysis of a solution by X-ray fluorescence.

This apparatus includes means (12, 14) for the excitation and analysis of the solution, means (4) for receiving the solution and an element (6) integral with the receiving means and positioned opposite an area of the receiving means which is transparent to the X-radiation, the element when it is excited, emitting an X-radiation distinct from that emitted by the solution, which allows any measurement drift that is liable to occur to be corrected during the analysis.

Application to the analysis of solutions containing actinides.

9 Claims, 3 Drawing Sheets

APPARATUS FOR THE ANALYSIS OF A SOLUTION BY X-RAY FLUORESCENCE

DESCRIPTION

1. Technical Field

This invention relates to an apparatus for the analysis of a solution by X-ray fluorescence.

It is notably applicable to the on-line X-ray fluorescence analysis of elements present in solution in small amounts.

The invention is most particularly applicable to the on-line analysis of solutions containing actinides, such as, for example, uranium and plutonium.

2. State of the Prior Art

Within plant used for the preparation, use or treatment of radioactive materials, it is necessary to know the concentrations of those materials which are present in solutions resulting from the different treatment processes.

This fact allows to know the performance of these processes and to avoid sending these materials to destinations where they would be undesirable.

The radioactive elements to be followed can be analyzed at present in a qualitative and quantitative manner by apparatus which uses the phenomenon of X-ray fluorescence.

In order to obtain a measurement of the concentration of these radioactive elements, it is possible to take a sample representative of a solution containing these elements.

In order to obtain a result more rapidly, it is possible to cause the solution to circulate directly in a measurement cell provided with a window which is transparent to X-rays.

On this subject, documents (1), (2) and (3) will be consulted, which like document (4) quoted below, are mentioned at the end of this description.

Known techniques allow to avoid two phase effects (see document (2)) but only in the case of high fluid flow rates.

Furthermore, the apparatus used for these known techniques are susceptible to more or less long term measurement drift, this drift being liable to bring about measurement errors.

The measurement is equally a function of the medium within which the elements to be analyzed are steeped.

In a way that gets rid of apparatus drift and medium variations, it is known to add to the solution to be analyzed, a specific amount of a known element which can be used as a reference.

On this subject reference is made to document (4)

In many cases of on-line analysis, it is not possible to add an element to the solution without disturbing the carrying out of a treatment process.

DESCRIPTION OF THE INVENTION

The aim of this invention is to remedy the previous disadvantage.

The invention allows avoid the effects of operating conditions which differ from those under which the calibration of the X-ray fluorescence apparatus has been carried out.

The invention is applicable to the on-line analysis of a single phase solution.

It permits measurement errors due to apparatus drift to be minimized and allows detection of medium variations or the presence of a gaseous phase in the solution to be analyzed, through the use of a reference element which is not in solution, so that the solution is not contaminated by this reference element.

To be precise, the object of this invention is an apparatus for the X-ray fluorescence analysis of a solution, this apparatus being characterized in that it includes:

excitation and analysis means, intended to excite the solution by an excitation X-radiation and to analyze an analysis X-radiation emitted by the solution thereby excited, means for receiving the solution, these receiving means including at least one area which is transparent to the excitation and analysis X-radiation, said excitation and analysis X-radiation passing through said at least one area;

a reference element exterior to the solution, integral with the receiving means, positioned opposite said area in such a way that the solution is between this area and this element, and capable of emitting a reference X-radiation distinct from the analysis X-radiation when this element receives the excitation radiation, said area being transparent to the reference radiation, this reference X-radiation being analyzed with the analysis X-radiation and making it possible to correct any measurement drift that is liable to occur during the analysis of the solution.

According to a first particular embodiment of the apparatus which is the object of the invention, the solution receiving means include a flow line within which the solution circulates and which is provided with a window transparent to the excitation, analysis and reference X-radiation, this window constituting said area, the reference element being made integral with this flow line.

This flow line can be fitted with a measurement cell which the solution is intended to pass through and which carries the window, the reference element being made integral with this measurement cell.

Preferably, at the place where the window is, this measurement cell has a small cross-sectional area through which the solution passes.

This allows renewal of the solution, even at a low flow rate, and hence the response time and clogging of the apparatus are minimized.

According to a second particular embodiment of the apparatus which is the object of the invention, the solution receiving means include a container which is intended to contain the solution and which is made of a material transparent to the excitation, analysis and reference X-radiation.

This container can be an X-ray fluorescence analysis receptacle.

Preferably, the reference element is a mechanical component made of a metallic material.

This component can be a screw.

In certain cases, notably for the analysis of a solution containing actinides, it is advantageous to use zirconium as a constituent material for this component.

BRIEF DESCRIPTION OF THE DRAWINGS

This invention will be better understood by reading the description of the examples of embodiments given below purely for information purposes and in no way limitative, whilst referring to the appended drawings in which.

DETAILED DESCRIPTION OF PARTICULAR EMBODIMENTS

Figure 1:
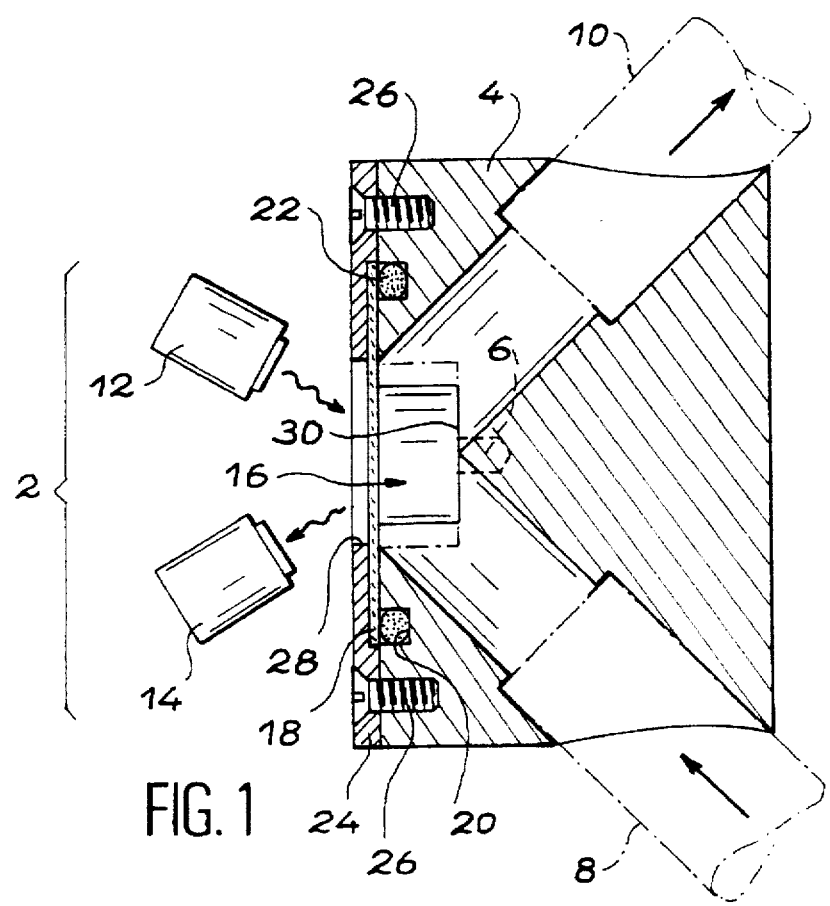
FIG. 1 is a diagrammatic section view of a particular embodiment of the apparatus which is the object of the invention.
Figure 2:
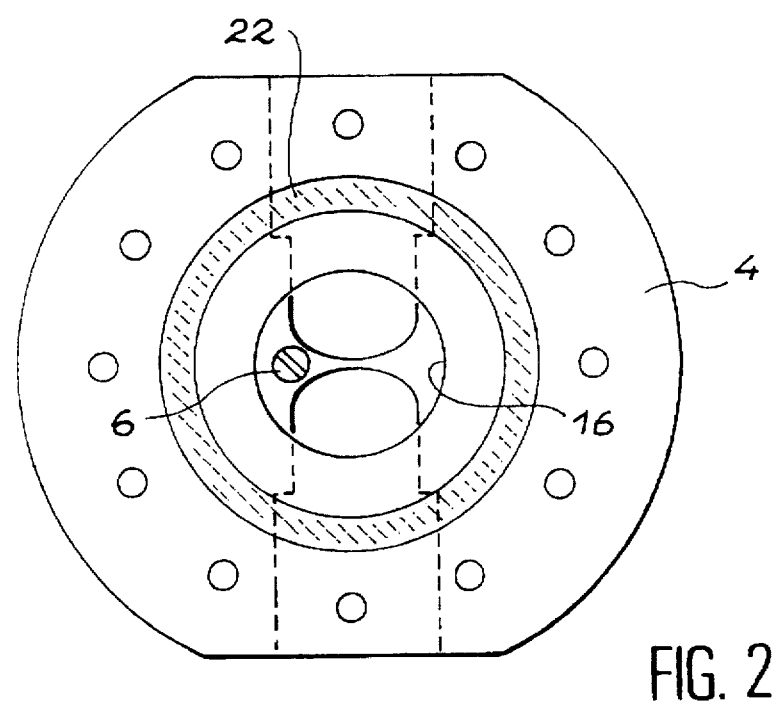
FIG. 2 is a front elevation of a measurement cell which is included in the apparatus in FIG. 1 and from which the window and the collar have been removed.

The apparatus conforming to the invention, which is represented schematically in section in FIG. 1, is intended for the on-line, X-ray fluorescence, analysis of a liquid solution.

This apparatus in FIG. 1 includes:

excitation and analysis means 2, a measurement cell 4, and a reference element 6.

The measurement cell 4 is mounted in a flow line within which the solution to be analyzed circulates and in FIG. 1, it can see a part of the cell 8, through which the solution enters the measurement cell and another part 10 through which the solution exits this measurement cell.

As far as the excitation and analysis means 2 are concerned, only the means 12 for the emission of the excitation X-radiation (an X-ray tube) and the means 14 for the detection of the fluorescence X-radiation (for example a semi-conductor) which are included in these excitation and analysis means, are represented in FIG. 1.

The measurement cell 4 comprises an opening 16 which allows passage of a beam of excitation X-radiation coming from the X-ray tube 12 and the return passage of a beam of fluorescence X-radiation coming from the elements (for example actinides such as uranium and plutonium) which are contained in the solution to be analyzed.

A spectrometer (not represented) allows analysis of the fluorescent X-radiation detected by the semi-conductor 14.

The minimum diameter of the opening 16 is determined by the useful diameter of the excitation beam and by the useful diameter of the fluorescence beam seen by the detection means.

The measurement cell 4 is also provided with a window 18 which is transparent to the excitation X-radiation, the fluorescence X-radiation, coming from the solution, and the reference X-radiation, emitted by the element 6 when this receives the excitation radiation.

For example, a window of boron carbide $B_4C$ or boron nitride or beryllium is used.

The measurement cell 4 is also provided with a circular groove 20 around the opening 16.

A toroidal sealing ring 22 is housed in this groove 20.

The window 18 rests against this seal.

This window 18 is held in this position by a collar 24 which presses against the window 18 and which is fixed to the measurement cell 4 by screws 26.

This collar 24 includes an opening 28 which is opposite the window 18 and through which the excitation and fluorescence X-radiation passes, the excitation and analysis means 2 being positioned opposite this opening 28.

The maximum diameter of the opening 16 which is included in the measurement cell 4 is determined by the maximum pressure that can be applied in the cell taking into account the mechanical properties of the X-ray transparent window 18.

The cross-sectional area through which the solution passes at this opening 16, is sufficiently small to allow rapid renewal of the solution and rapid solution homogenization when a change in the concentration of the elements present in this solution occurs.

This cross-sectional area for passage of the solution is of the order of the size of the cross-sectional area of the solution inlet pipe (part 8) or the cross-sectional area of the solution outlet pipe (part 10).

This also allows clogging up to be minimized at the place where the measurement is carried out, thanks to a raised fluid flow speed.

For a single phase solution, the performance of the apparatus in FIG. 1, in terms of response time at flow rates less than 50 liters per hour is maintained.

It should be noted that the window 18, for example in the shape of a disc, together with the seal 22, also ensures the sealing of the opening 16 of the measurement cell 4.

It is specified that the diameter of the opening 28 of the collar 24 and the diameter of the toroidal sealing ring 22 are sufficiently small to allow the measurement cell 4 to hold pressure well.

Furthermore, the collar 24 has a capacity for absorbing X-rays that is sufficient to prevent deterioration of the toroidal sealing ring 22 by the X-rays ensuring that the measurement cell 4 is sealed.

It should be noted that assembly and disassembly of the window 18 and the seal 22 are made easy, when it is desired to carry out an operation on the measurement cell 4 (for example, to change the window or this seal).

In the case of an analysis using an energy dispersive X-ray spectrometer, a drift in signal amplification can occur.

This drift is expressed by a displacement in the energy of the X-ray fluorescence spectrum obtained.

By having a reference peak at ones disposal, this amplification drift can be observed and used to reset the energy spectrum, particularly the peaks coming from fluorescence lines which are close to the reference line.

The reference peak is given by the reference element 6.

In the example in FIG. 1, this reference element is in the form of a screw (in zirconium for the examples given further below).

This screw 6 is fixed to the measurement cell, opposite the opening 16, at the bottom of the cavity 30 which is formed in the body of the measurement cell 4 and which connects with pipes 8 and 10, this cavity being provided with opening 16.

The screw 6 receives the excitation X-radiation and the fluorescence X-radiation emitted by this screw 6 is seen by the detection means The diameter of the screw, its length and its position are chosen so that the fluorescence signal coming from this screw is sufficiently high to be seen in a meaningful way by the detection means without, however, saturating them.

As a variant, instead of one component, a powder of an appropriate material (zirconium powder in the examples given further below) can be used, encapsulated in a material transparent to X-rays.

In the case of an energy dispersive spectrometer, the intensity of the reference peak must be sufficient for the error on the peak due to counting statistics to be at least less than the error sought in the result.

In addition, the intensity of the reference peak must not disturb the analysis of the peaks from the elements to be analyzed, by peak to peak interference or by too high a number of counts being received by the detection means which would cause their saturation.

This reference peak must be a peak from a chemical element that is not desirable to analyze whilst being close to peaks of elements in the solution, the desired concentrations.

In the case of an analysis by X-ray fluorescence of elements at low concentration carried out by taking a sample, a reference element can also be placed after the excitation means and the sample, being seen by the detection means in a way that gives information about the medium in which the elements are and about the presence or not of a gaseous phase.

It should be noted that, according to the nature of the medium of the solution that can be analyzed, it is possible to optimize the geometric characteristics and the distance of the screw 6 from the window 18 in order to improve the sensitivity of detection of variations in the density of this medium.

As an example, it can be considered a procedure for the reprocessing of irradiated fuel where it is desirable to analyze the heavy elements uranium and plutonium present at low concentration in aqueous and organic media.

In this case, the observation of X-ray fluorescence lines for these elements—the $L\alpha1$ and $L\alpha2$ lines—can permit an elemental analysis.

The $K\alpha1$ and $K\alpha2$ lines from zirconium are sufficiently far away from the $L\alpha$ lines of the heavy elements mentioned above for these lines not to interfere.

But they are sufficiently close to them to appear in the analysis window of the detection means and to allow the resetting of energy spectrum.

Figure 3:
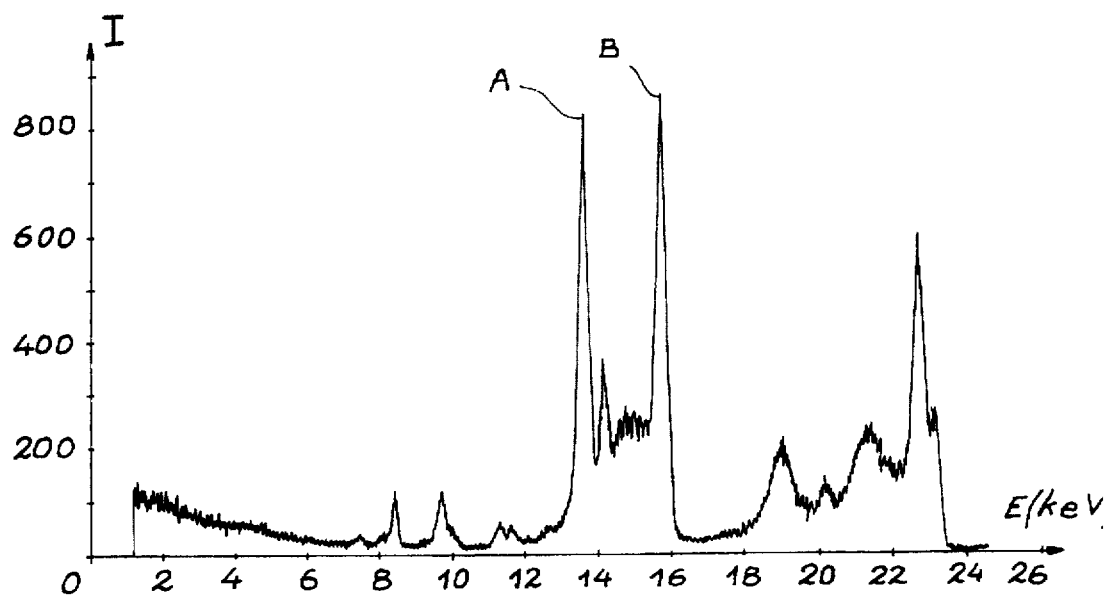
FIG. 3 is an X-ray fluorescence spectrum of a uranium solution with a zirconium reference.

FIG. 3 shows the spectrum obtained with a solution of uranium irradiated by a flux of X-photons coming from an X-ray tube.

On the x-axis are the energies E expressed in KeV and on the y-axis the intensity I expressed as the number of counts.

Peak A corresponds to uranium and peak B to zirconium.

The detection means that allow to obtain this spectrum include a normal energy dispersive spectrometer or any type of apparatus that allows the energy discrimination of the lines (X) of the elements.

Between the sample and the spectrometer diode, there is an input diaphragm and an energy filter.

The element zirconium, being used as a reference, is excited by the X-ray tube.

It supplies a constant X-ray fluorescence signal if the X-ray tube has a constant intensity and if the medium does not vary.

If there is no variation in the solution medium, a simple ratio of the intensity of the peak to be analyzed (peak A from the uranium) to that from the reference peak (peak B from the zirconium) allows to avoid the effects of fluctuations in the excitation source (the X-ray tube).

The measurement of the concentration of an element is carried out by comparison with standard solutions.

In a first step, a standardization is carried out with standard solutions.

The signal that is considered is the ratio of the intensity from the element to be determined to the intensity from the reference element.

Coefficients taken from the calibration line allow determination of the concentration of an unknown solution.

The case of an apparatus where the excitation source is an X-ray tube will be considered.

Figure 4:
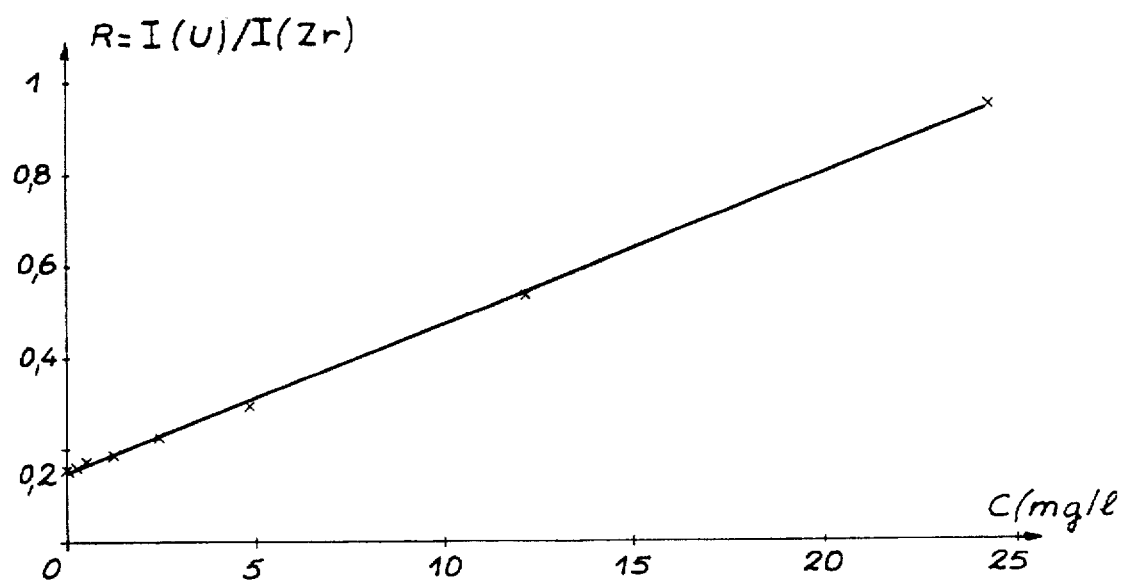
FIG. 4 represents a straight calibration line obtained with an apparatus conforming to the invention.

FIG. 4 shows the calibration line obtained by taking the ratio R of the intensity of the uranium signal I(U) to the intensity of the zirconium signal I(Zr).

On the x-axis is the concentration of uranium C expressed in mg/l.

On the y-axis is the ratio R mentioned above.

This ratio R allows to avoid the effects of any fluctuations of the X-ray tube.

Figure 5:
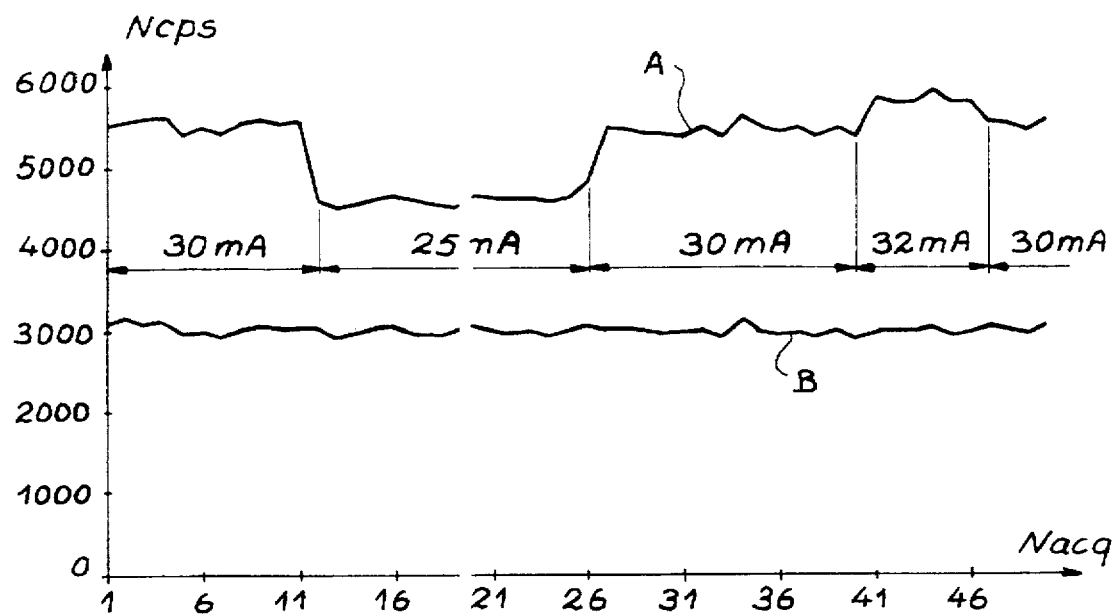
FIG. 5 shows variations of a signal in relation to the uranium contained in an analyzed solution and of a uranium/ zirconium ratio for different current intensities of the X-ray tube for an apparatus conforming to the invention.

FIG. 5 shows the variations of the intensity relative to the uranium, expressed as the number of counts Ncps, as a function of the number of the acquisition Nacq (curve A) and the variation of the ratio R mentioned above, multiplied by 10000, as a function of the number of the acquisition (curve B).

The X-ray tube current intensity (expressed in mA) has also been noted on FIG. 5.

As FIG. 5 shows, the signal coming from the uranium is a function of the variation of the intensity from the X-ray tube.

On the other hand, the ratio R stays constant to within statistical fluctuations.

This ratio is independent of variations in the intensity from the X-ray tube.

In the case of medium variations, if these are known, it is possible to do the same thing to be free of the effects of variations in the excitation source the X-ray tube).

Nevertheless, it is necessary to take this into account during calibration which must cover the whole range of solution media to be analyzed.

If the solution is not homogeneous and includes a gaseous phase, the X-photons coming from the X-ray tube penetrate more deeply into the solution.

They excite the reference element 6, situated at the bottom of the cavity 30 of the measurement cell 4, more intensely and the fluorescence X-photons coming from this element are absorbed less in the gaseous phase.

The intensity of the reference peak is accordingly greater.

On the other hand, the gaseous phase, having the effect of decreasing the apparent concentration of the solution, the intensity of the X-ray fluorescence lines of the elements in the solution decreases.

Hence, a gaseous phase in a solution has opposite effects on the intensities of the X-ray fluorescence lines:

the intensities of the lines relative to the elements to be analyzed in solution decrease, the intensities of the lines relative to the reference element increase.

Simultaneous observation of the intensities of these lines can therefore give information on phase variations of the solution.

This is a means of control that allows the presence of a gaseous phase which can falsify the measurement to be noted.

Figure 6:
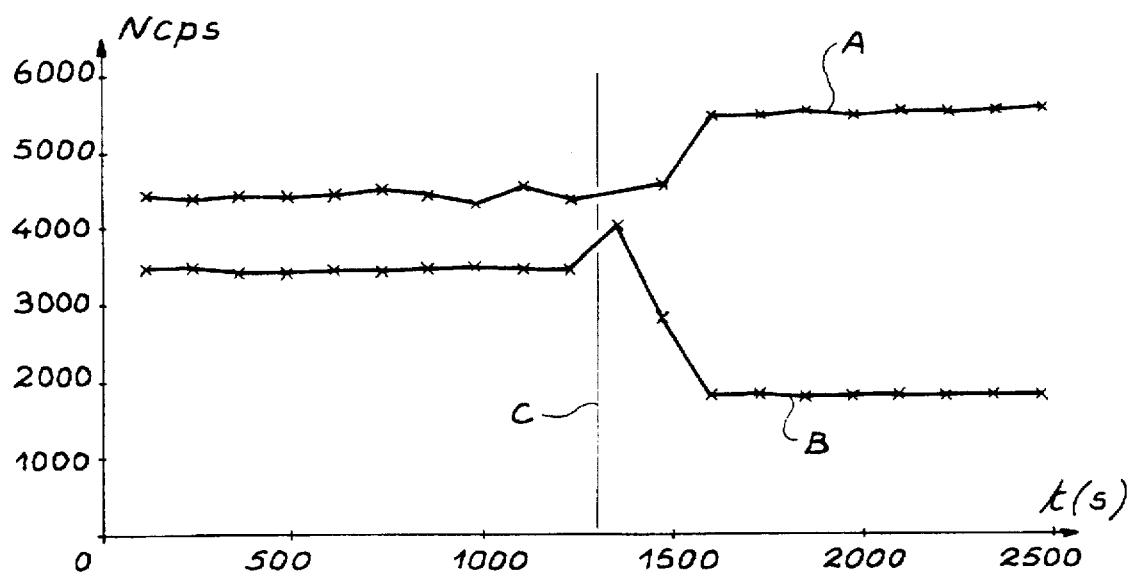
FIG. 6 shows measurements made with and without a gaseous phase passing within the measurement cell of an apparatus conforming to the invention.

FIG. 6 shows the variations, as a function of time t (expressed in seconds), of signals (expressed as a number of counts Ncps) in relation to the uranium (curve A) and to the zirconium (curve B); in order to allow the variations in the intensities in relation to the uranium and to the zirconium to be shown on the same graph, the intensity relative to the zirconium has been divided by 10.

The measurements have been carried out with a gaseous phase being passed into the measurement cell and without a gaseous phase being passed into the measurement cell.

The vertical line C in FIG. 6 shows the end of introduction of the gaseous phase.

Thus, the part of FIG. 6 situated to the left of this line C corresponds to a gaseous phase being passed into the measurement cell and the part of FIG. 6 situated to the right of line C corresponds to the absence of any gaseous phase being passed into the measurement cell.

FIG. 6 shows the variations, in opposite directions, of the signal coming from the element to be analyzed and of the signal coming from the reference element, in the case where a gaseous phase is introduced into the measurement cell.

The invention is also applicable to X-ray fluorescence analysis of a solution contained in any type of container having sufficient transparency to X-rays of energy within the range corresponding to the excitation and analysis means and notably may be contained in any usual receptacle used for X-ray fluorescence analysis.

The documents which have been mentioned in this description are the following:

(1) "Selection and testing of materials for use in a flow-through liquid sampling cell for X-ray fluorescence analysis of special nuclear materials in dissolver solution", C. R. HUDGENS, U.S. DEPARTMENT OF ENERGY, MONSANTO RESEARCH CORPORATION, August 1984

(2) FRENCH PATENT APPLICATION No. 94 04225 of the 11th April 1994 "Appareil pour l'analyse en ligne de produits fluides polyphasés (An apparatus for the on-line analysis of polyphase fluid products)", M. MERELLI, J. LAVERGNE, G. LAMARQUE, G. MUS, COMMISSARIAT A L'ENERGIE ATOMIQUE=FR-A-2 718 528

(3) "Development of on line energy dispersive X-ray fluorescence to monitor actinide contaminated waste stream", R. S. DAY, A. R. VIGIL, American Nuclear Society, International Topical Conference, Methods and Applications of Radioanalytical Chemistry, HAWAII, April 1994

(4) "La spectrométrie de fluorescence X a reflexion totale (TXRF) : une méthode d'avenir pour la micro-analyze d'échantillons radioactifs (Total reflection X-ray fluorescence spectrometry (TXRF); a future method for the microanalysis of radioactive samples)", Ph. BIENVENU, P. TRABUC, Ph. LLUG, R. JOUEN, CEA CADARACHE, CETAMA "Analyze non destructive (Non-destructive analysis)", A collection of communications presented during technical discussion days 29th and 30th Sep. 1993 at the Centre d'études, Valduc.

We claim:

1. An apparatus for the analysis of a solution by X-ray fluorescence, this apparatus being characterized in that it includes;

excitation and analysis means (12, 14), intended to excite the solution by an excitation X-radiation and to analyze an analysis X-radiation emitted by the solution thereby excited, means (4, 8, 10) for receiving the solution, these receiving means including at least one area (18) which is transparent to the excitation and analysis X-radiation, said excitation and analysis X-radiation passing through said at least one area, a reference element (6) exterior to the solution, integral with the receiving means, positioned opposite said area in such a way that the solution is between this area and this element, and capable of emitting a reference X-radiation distinct from the analysis X-radiation when this element receives the excitation radiation, said area being transparent to the reference radiation, this reference X-radiation being analyzed with the analysis X-radiation and making it possible to correct any measurement drift that is liable to occur during the analysis of the solution.

2. An apparatus according to claim 1, characterized in that the receiving means include a flow line (8, 10) within which the solution circulates and which is provided with a window (18) transparent to the excitation, analysis and reference X-radiation, this window constituting said area, the reference element being made integral with this flow line.

3. An apparatus according to claim 2, characterized in that the flow line is provided with a measurement cell (4) which the solution is intended to pass through and having the window (18), the reference element being made integral with this measurement cell.

4. An apparatus according to claim 3, characterized in that at the place where the window (18) is, the measurement cell (4) has a small cross-sectional area through which the solution passes.

5. An apparatus according to claim 1, characterized in that the receiving means include a container which is intended to contain the solution and which is made of a material transparent to the excitation, analysis and reference X-radiation.

6. An apparatus according to claim 5, characterized in that this container is an X-ray fluorescence analysis receptacle.

7. An apparatus according to claim 1, characterized in that the reference element is a mechanical component (6) made of a metallic material.

8. An apparatus according to claim 7, characterized in that this component is a screw (6).

9. An apparatus according to claim 7, characterized in that the material is zirconium.

* * * * *